(12) United States Patent
Kugler et al.

(10) Patent No.: US 10,390,849 B2
(45) Date of Patent: Aug. 27, 2019

(54) CAPTURE ASSEMBLY AND METHOD

(71) Applicant: Teleflex Innovations S.à.r.l., Luxembourg (LU)

(72) Inventors: Chad Kugler, Buffalo, MN (US); Steve Michael, New Hope, MN (US); Alexander Marine, Excelsior, MN (US)

(73) Assignee: Teleflex Innovations S.à.r.l., Luxembourg (LU)

( * ) Notice: Subject to any disclaimer, the term of this patent is extended or adjusted under 35 U.S.C. 154(b) by 117 days.

(21) Appl. No.: 15/148,038

(22) Filed: May 6, 2016

(65) Prior Publication Data

US 2016/0242798 A1   Aug. 25, 2016

Related U.S. Application Data

(63) Continuation of application No. 14/849,774, filed on Sep. 10, 2015, now Pat. No. 9,351,747.
(Continued)

(51) Int. Cl.
*A61B 17/22* (2006.01)
*A61M 1/00* (2006.01)
(Continued)

(52) U.S. Cl.
CPC ........ *A61B 17/22031* (2013.01); *A61B 17/22* (2013.01); *A61B 17/3207* (2013.01);
(Continued)

(58) Field of Classification Search
CPC ........... A61B 2017/22079; A61B 2017/22035; A61B 2017/22001; A61B 2017/22039;
(Continued)

(56) References Cited

U.S. PATENT DOCUMENTS 4,654,027 A * 3/1987 Dragan ........... A61M 25/10185
137/614.2
4,820,270 A    4/1989 Hardcastle et al.
(Continued)

FOREIGN PATENT DOCUMENTS

DE       1092161 B      11/1960
DE    19638058 A1       3/1997
(Continued)

OTHER PUBLICATIONS

Applicant's Response filed May 13, 2016 to Written Opinion dated Nov. 9, 2015 in connection with PCT Application No. PCT/US2015/049299 filed Sep. 10, 2015.
(Continued)

*Primary Examiner* — Shaun L David
(74) *Attorney, Agent, or Firm* — Gregory W. Smock

(57) ABSTRACT

This patent document discloses assemblies and methods for removing obstructive material from a body vessel or other cavity. An assembly can include an elongate inner member, an elongate outer member, an aspirator, one or more valves, or a waste collection reservoir. Each of the elongate members can extend from a proximal end portion to a distal end portion and can include a lumen therethrough. The elongate inner member can be partially disposed in the lumen of the elongate outer member and can be moveable along its longitudinal axis relative to the elongate outer member. The aspirator can be in flow communication with the proximal end portion of the elongate inner member for drawing the obstructive material into or through its lumen. The one or more valves can be configured and positioned to allow obstructive material removed from the body vessel or cavity to be urged toward the waste collection reservoir.

17 Claims, 7 Drawing Sheets

Related U.S. Application Data

(60) Provisional application No. 62/048,736, filed on Sep. 10, 2014.

(51) Int. Cl.
*A61M 5/315* (2006.01)
*A61B 17/3207* (2006.01)
*A61M 25/00* (2006.01)
*A61M 25/09* (2006.01)

(52) U.S. Cl.
CPC ...... *A61M 1/0035* (2014.02); *A61M 5/31511* (2013.01); *A61M 25/005* (2013.01); *A61M 25/09* (2013.01); *A61B 2017/22038* (2013.01); *A61B 2017/22039* (2013.01); *A61B 2017/22041* (2013.01); *A61B 2017/22079* (2013.01); *A61B 2017/22094* (2013.01); *A61B 2217/005* (2013.01)

(58) Field of Classification Search
CPC .............. A61B 17/22; A61B 17/22012; A61B 17/22031; A61B 17/22032; A61B 17/32; A61B 17/3203; A61B 17/32037; A61B 17/32053; A61B 17/3207; A61B 17/320708; A61B 17/32075; A61B 17/320758; A61M 2025/0037; A61M 2025/0681; A61M 2025/0687
See application file for complete search history.

(56) References Cited

U.S. PATENT DOCUMENTS

| | | | |
|---|---|---|---|
| 4,863,440 A | 9/1989 | Chin | |
| 5,011,488 A | 4/1991 | Ginsburg | |
| 5,338,294 A | 8/1994 | Blake | |
| 5,356,375 A * | 10/1994 | Higley | A61M 5/36 604/142 |
| 5,941,869 A * | 8/1999 | Patterson | A61B 17/3207 604/22 |
| 5,989,210 A | 11/1999 | Morris et al. | |
| 6,053,923 A * | 4/2000 | Veca | A61B 17/32002 606/79 |
| 6,142,987 A * | 11/2000 | Tsugita | A61F 2/01 604/500 |
| 6,767,353 B1 | 7/2004 | Shiber | |
| 6,818,001 B2 * | 11/2004 | Wulfman | A61B 17/320758 606/159 |
| 7,041,084 B2 | 5/2006 | Fojtik | |
| 7,833,240 B2 | 11/2010 | Okushi et al. | |
| 8,162,877 B2 | 4/2012 | Bonnette et al. | |
| 8,795,219 B1 | 8/2014 | Al-Rashdan | |
| 8,858,585 B2 | 10/2014 | Stengel | |
| 9,005,154 B2 | 4/2015 | Matson et al. | |
| 9,078,682 B2 | 7/2015 | Lenker et al. | |
| 2007/0083158 A1 | 4/2007 | Hirszowicz et al. | |
| 2007/0135832 A1 * | 6/2007 | Wholey | A61F 2/013 606/200 |
| 2008/0243153 A1 * | 10/2008 | Nguyen | A61B 17/32037 606/159 |
| 2010/0016792 A1 | 1/2010 | Hirszowicz | |
| 2010/0022970 A1 | 1/2010 | Hirszowicz | |
| 2010/0030186 A1 * | 2/2010 | Stivland | A61B 17/22 604/510 |
| 2010/0036410 A1 | 2/2010 | Krolik et al. | |
| 2010/0249815 A1 | 9/2010 | Jantzen et al. | |
| 2011/0034937 A1 | 2/2011 | Mustapha et al. | |
| 2011/0224642 A1 * | 9/2011 | Fojtik | A61M 5/204 604/500 |
| 2013/0035628 A1 | 2/2013 | Garrison et al. | |
| 2013/0178790 A1 * | 7/2013 | Tekulve | A61M 25/007 604/28 |
| 2013/0345787 A1 | 12/2013 | Igaki et al. | |
| 2015/0005781 A1 | 1/2015 | Lund-Clausen et al. | |

FOREIGN PATENT DOCUMENTS

| | | |
|---|---|---|
| EP | 2921122 A1 | 9/2015 |
| GB | 1588072 A | 4/1981 |
| GB | 2501490 A | 10/2013 |
| JP | 2013183951 A | 9/2013 |
| WO | 1999045835 A2 | 9/1999 |
| WO | 2007004221 A1 | 1/2007 |
| WO | 2010001405 A1 | 1/2010 |

OTHER PUBLICATIONS

Second Written Opinion dated Aug. 8, 2016 in connection with PCT Appln. No. PCT/US2015/049299 filed Sep. 10, 2015.

Applicant's Response filed Aug. 17, 2016 to Second Written Opinion dated Aug. 8, 2016 in connection with PCT Application No. PCT/US2015/049299 filed Sep. 10, 2015.

International Search Report dated Nov. 9, 2015 in corresponding PCT Appln. No. PCT/US2015/049299 filed Sep. 10, 2015.

Written Opinion mailed 9 Nov. 2015 in PCT Appin. No. PCT/US2015/049299 filed 10 Sep. 2015.

\* cited by examiner

CAPTURE ASSEMBLY AND METHOD

CLAIM OF PRIORITY

This non-provisional patent document is a continuation of U.S. patent application Ser. No. 14/849,774, entitled "CAPTURE ASSEMBLY AND METHOD" and filed Sep. 10, 2015, which claims the benefit of priority under 35 U.S.C. § 119(e) to U.S. Provisional Patent Application Ser. No. 62/048,736, entitled "THROMBECTOMY ASSEMBLY AND METHOD" and filed on Sep. 10, 2014, both of which are herein incorporated by reference in their entirety.

TECHNICAL FIELD

This patent document relates to medical devices. More particularly, but not by way of limitation, the patent document relates to object capture assemblies and methods of capturing and removing objects from a body lumen, particularly for the capture and removal of obstructive material from a patient's vasculature.

BACKGROUND

Occlusive diseases of the vasculature are a leading cause of mortality and morbidity. While the nature of vascular diseases varies greatly, the underlying clinical cause is a reduction in blood flow due to an accumulation of obstructive material in one or more vessels feeding or draining an affected organ. The obstructive material can vary in hardness and composition. Harder obstructive material often contains calcified atherosclerotic plaque, whereas softer obstructive material often contains blood clots (thrombi), and vascular disease is commonly caused by a combination of the two.

Obstructive material is often found in the peripheral circulatory system as well as the coronary vessels. When such obstructions develop abruptly in one or more coronary vessels feeding the heart, a heart attack can occur. When obstructions develop over a longer period in one or more coronary vessels, patients can experience angina; while developing obstructions in one or more peripheral vessels can result in patient pain, ulcers, or gangrene in an extremity. When the blockage of blood flow becomes sufficiently serious, it is necessary to intervene and recanalize the affected blood vessel(s).

OVERVIEW

Clinical treatment of vascular disease can involve surgical, pharmaceutical, or catheter-based therapies. Surgical methods for treating vascular occlusive disease tend to be highly invasive and are typically associated with long hospital stays and high costs. Pharmaceutical treatment using dissolving drugs takes time to work, can inadvertently cause bleeding elsewhere in a patient's body, and can undesirably dislodge large particles of obstructive material. Catheter-based therapies use various mechanisms to fragment, displace or remove vascular obstructions and offer shortened procedure times and reduced hospital stays.

The present inventors recognize that traditional catheter-based therapies have many shortcomings. For example, traditional catheter-based therapies configured to break down obstructive material prior to aspiration require expensive capital equipment (such as a motor-turned wire or ultrasonic waves) and routine maintenance. Many other traditional catheter-based therapies seek to remove obstructive material without first breaking it down, which can lead to the catheter becoming plugged with obstructive material and having to be removed from the treatment site and cleaned before continued use. The present inventors further recognize that traditional catheter-based therapies for removing obstructive material have limited suction profiles or suction power.

The present assemblies provide a single, disposal tool for breaking down, capturing, and removing obstructive material without requiring expensive capital equipment or maintenance. The assemblies can be used to remove a number of obstructive materials from a number of different treatment sites within a patient's body before being removed. An assembly can include an elongate inner member, an elongate outer member, an aspirator, one or more valves, and a waste collection reservoir. Each of the elongate members can extend from a proximal end portion to a distal end portion and can include a lumen therethrough. The elongate inner member can be partially disposed in the lumen of the elongate outer member and can be moveable along its longitudinal axis relative to the elongate outer member. The aspirator can be in flow communication with the proximal end portion of the elongate inner member for drawing the obstructive material into or through its lumen. The one or more valves can be configured and positioned to allow obstructive material removed from the body to be urged toward the waste collection reservoir.

The present methods provide steps for breaking down, capturing, and removing obstructive material from a body vessel or cavity. A method can include percutaneously advancing a distal end of an assembly, including an elongate inner member and a surrounding elongate outer member, to a location proximate to the obstructive material to be removed. The elongate inner member can be moved relative to the elongate outer member along its longitudinal axis to break down the obstructive material and/or to draw the occlusive material into a lumen of the elongate inner member. An aspirator, in flow communication with a proximal end of the elongate inner member, can be activated to capture and remove the obstructive material through the lumen of the elongate inner member and direct the material to a waste collection reservoir.

These and other examples and features of the present assemblies and methods will be set forth in the following Detailed Description. This Overview is intended to provide non-limiting examples of the present subject matter—it is not intended to provide an exclusive or exhaustive explanation. The Detailed Description below is included to provide further information about the present assemblies and methods.

BRIEF DESCRIPTION OF THE DRAWINGS

In the drawings, like numerals can be used to describe similar features and components throughout the several views. The drawings illustrate generally, by way of example, but not by way of limitation, embodiments discussed in the present patent document.

Figure 1A:
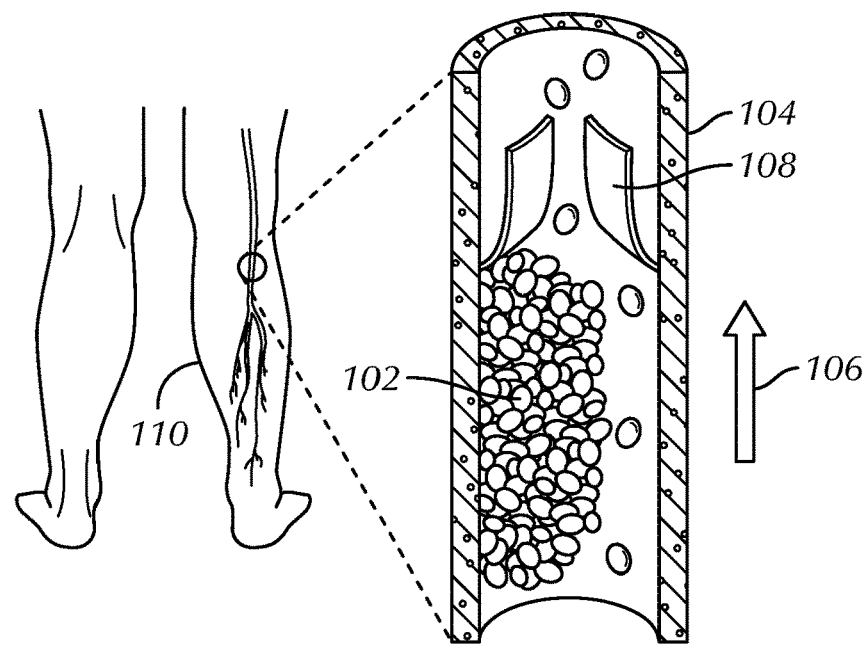
FIGS. 1A-B respectively illustrate schematic views of obstructive material formations within a deep peripheral vein and a pulmonary artery.

The drawing figures are not necessarily to scale. Certain features and components may be shown exaggerated in scale or in schematic form and some details may not be shown in the interest of clarity and conciseness.

DETAILED DESCRIPTION

The present assemblies and methods provide a single tool to aspirate a vessel or other cavity of a patient without the need for surgical intervention. When obstructive material is too large to be pulled into the lumen of an elongate inner member using proximally-created suction (negative pressure) alone, a first assembly embodiment allows an elongate inner member to be moved relative to a surrounding elongate outer member to break down the material's size. A combination of suction and shearing can be performed together or serially so that the obstructive material can be removed from the vessel or cavity and directed to a waste collection reservoir. According to a second assembly embodiment, an elongate inner member can be moved relative to a surrounding elongate outer member to create suction at a distal end portion of the assembly. This suction, alone or in combination with proximally-created suction, can be used to pull the obstructive material into and through the elongate inner member and ultimately direct it to a waste collection reservoir.

Figure 1B:
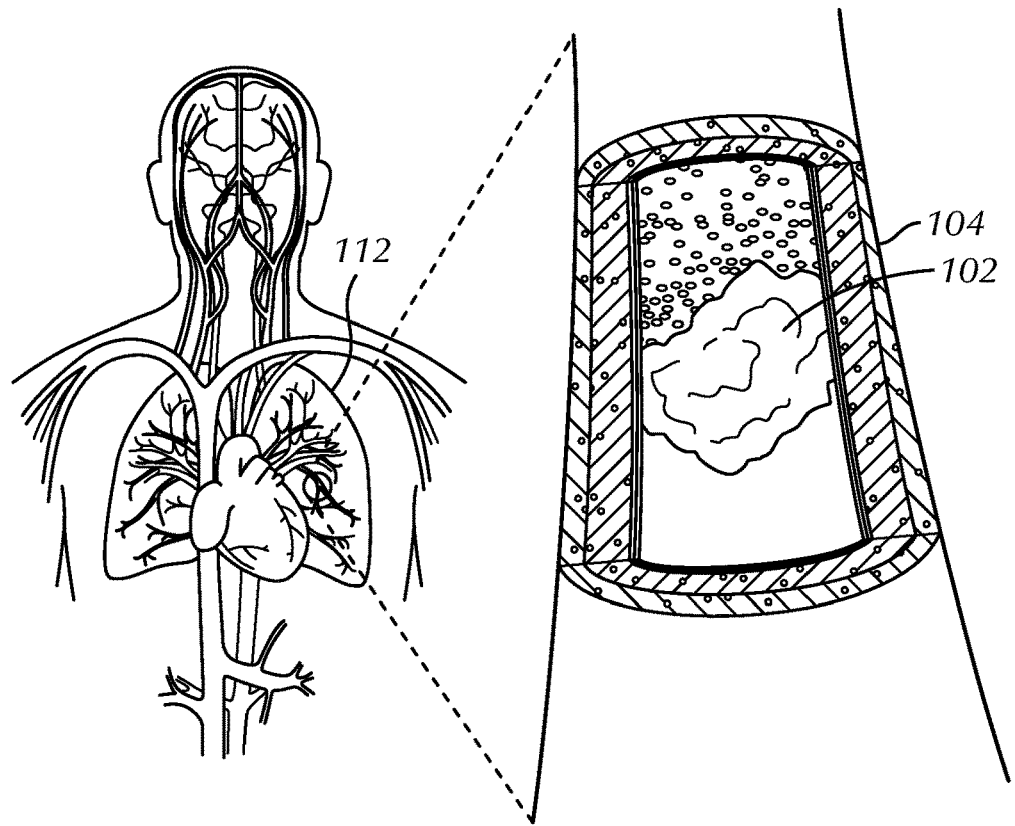

FIGS. 1A-B illustrate schematic views of obstructive material 102 formations within a vessel 104 (vein or artery) that can be aspirated using the present assemblies and methods. FIG. 1A illustrates a deep vein thrombosis (DVT) that can occur when obstructive material 102 in the form of a blood clot forms in one or more deep veins 104 of a patient's body. In the example shown, the blood clot can form below a venous valve 108 in a leg 110. Deep vein thrombosis is a serious condition that, if left untreated, can partially break loose, travel through the bloodstream in a direction 106 toward the patient's heart and lodge in the pulmonary artery 104 of a lung 112, blocking blood flow and causing a pulmonary embolism (PE), as illustrated in FIG. 1B. Pulmonary embolisms can be life-threatening, but prompt treatment can greatly reduce the risk of death. Taking measures to aspirate blood clots in the legs 110 can help protect against PE. While the present assemblies and methods can find use in the treatment of DVT and PE, it is to be understood that use of the assemblies and methods is not limited to deep veins or pulmonary arteries and can be used to aspirate vessels and cavities throughout the body.

Figure 2:
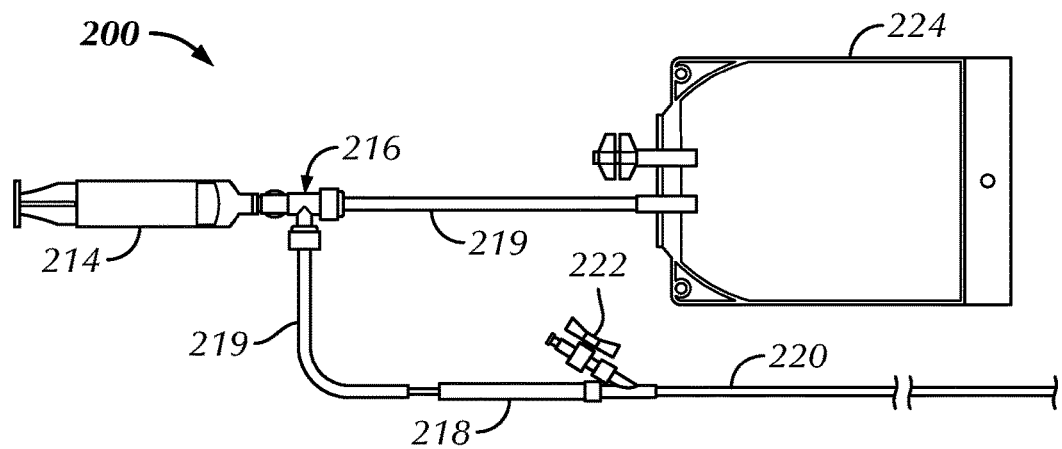
FIG. 2 illustrates an assembly for one or more of breaking down, capturing, and removing obstructive material from a vessel, as constructed in accordance with at least one embodiment.

FIG. 2 illustrates an assembly 200 for one or more of breaking down, capturing, and removing obstructive material from a vessel. The assembly can include an elongate outer member 220, an elongate inner member 218, an aspirator 214, a valve manifold 216, and a waste collection reservoir 224. Each of the elongate inner 218 and outer 220 members can extend from a proximal end portion to a distal end portion and can include a lumen therethrough. The elongate inner member 218 can be partially disposed in the lumen of the elongate outer member 220 and can be movable along its longitudinal axis relative to the elongate outer member 220. The aspirator 214 and the valve manifold 216 can be in flow communication with the proximal end portion of the elongate inner member 218 and the waste collection reservoir 224 for selectively drawing the obstructive material through the lumen of the elongate inner member 218 and directing such material to the waste collection reservoir 224. Extension tubing 219 can be used to facilitate these connections. A one-way valve in communication with the lumen of the elongate inner member 218 and allowing flow in a distal-to-proximal direction toward the aspirator 214 can be located within the valve manifold 216 (see FIG. 3) or the distal end portion of the elongate outer member 220 (see FIGS. 6A-C).

The elongate inner 218 and outer 220 members can have shapes that are sized and configured to facilitate their relative movements and placement within the vessel. The elongate inner member 218 can have a tubular shape with an outer diameter sized so that it can be inserted into the lumen of a tubular elongate outer member 220. The outer layer of the elongate inner member 218 and the inner layer of the elongate outer member 220 can be composed of low-frictional materials such as polytetrafluoroethylene (PTFE). At least the elongate outer member 220 can include a reinforcing layer composed of braided or wound fibers, strands or wraps for added pushability and torque strength. A radiopaque marker band or other externally visible component can be located on one or both of the elongate inner 218 and outer 220 members, such as in close proximity to their distal end portions for positioning purposes. The distal end portions of the elongate members 218, 220 can be composed of a flexible plastic material that minimizes mechanical trauma to the treated vessel. Optionally, the elongate outer member 220 can include a pre-curved configuration in its unbiased state to conform to a vessel or other body cavity in which the assembly 200 is to be positioned.

The assembly 200 can be percutaneously introduced into the vessel and advanced such that its distal end portion can be located proximate to obstructive material to be aspirated and its proximal end portion can be located outside the patient's body. The length of the assembly 200, and particularly the elongate inner 218 and outer 220 members, can depend upon a desired application. For example, elongate member lengths in the range of 120 cm to 140 cm or more can be used in femoral access percutaneous transluminal coronary applications. Intracranial and other applications may call for different elongate member lengths depending upon the vascular access site used. A stopcock 222 at the proximal end portion of the elongate outer member 220 can be used to flush portions of the assembly before, during or after its introduction within the body.

Figure 3:
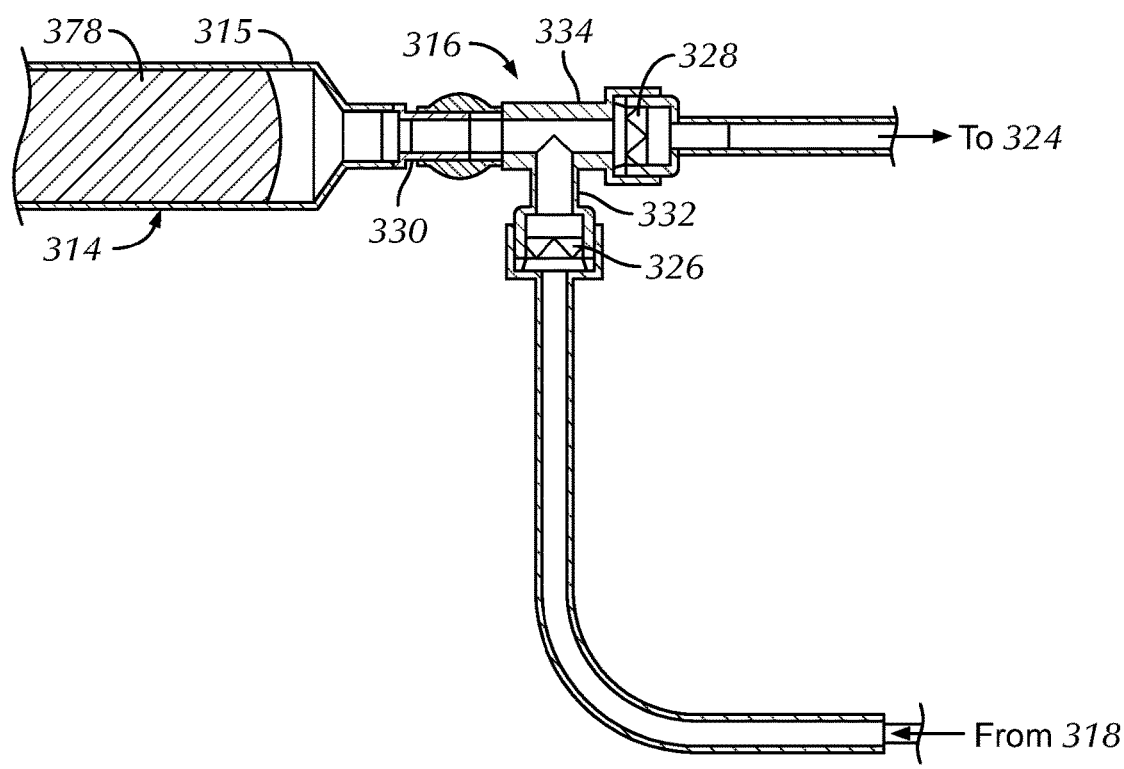
FIG. 3 illustrates a valve manifold for directing negative and positive pressures created by an assembly, as constructed in accordance with at least one embodiment.

FIG. 3 illustrates a cross-section of a valve manifold 316 as constructed for use with at least one embodiment of the present assemblies. The valve manifold 316 can direct negative pressure created by an aspirator 314 through a lumen of an elongate inner member 318 and can further direct positive pressure created by the aspirator 314 on the obstructive material removed from a vessel and direct it to a waste collection reservoir 324. The valve manifold 316 can be configured to allow single operator control over the present assemblies, can be used for multiple obstructive material withdrawals during a single procedure, and can be made from materials that make it cost effective for disposal.

The valve manifold 316 can include first 332, second 334 and third 330 ports. The first port 332 can be attached to a proximal end portion of the elongate inner member 318. The second port 334 can be attached to the waste collection reservoir 324. The third port 330 can be attached to the aspirator 314. The aspirator can include a plunger 378 and a syringe barrel 315. The plunger 378 can be slidable in the syringe barrel 315 for producing the necessary negative and positive pressures to remove obstructive material from the vessel or cavity via the first port 332 and direct such material to the second port 334 and the waste collection reservoir 324.

The valve manifold 316 can further include first 326 and second 328 one-way valves. The first 326 and second 328 one-way valves can be positioned within the first 332 and second 334 ports, respectively. The first one-way valve 326 can be configured to move from a closed position to an open position in response to a predetermined negative pressure level created by the aspirator 314 through retraction (or proximal movement) of a plunger 378 and directed to the lumen of the elongate inner member 318. When opened, obstructive material and bodily fluid can be permitted to enter a distal end portion of the elongate inner member 318 and flow proximally into the syringe barrel 315 of the aspirator 314. The second one-way valve 328 can be configured to move from a closed position to an open position in response to a predetermined positive pressure level created by advancement (or distal movement) of the plunger 378, which urges collected obstructive material and bodily fluid from the aspirator 314 toward the waste collection reservoir 324. Alternatively, the first one-way valve can be positioned within a distal end portion of an elongate outer member, adjacent and distal to the distal end portion of the elongate inner member, such that the valve manifold 316 solely includes the second one-way valve 328 (see FIGS. 6A-C).

Figure 4A:
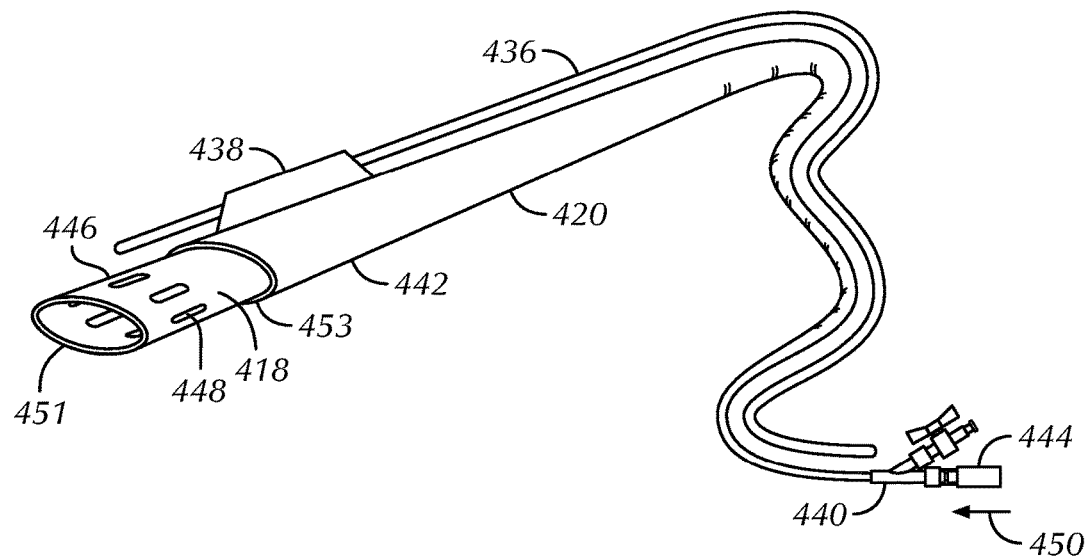
FIGS. 4A-B illustrate schematic views of relative movements between an elongate inner member and an elongate outer member, as constructed in accordance with at least one embodiment.
Figure 4B:
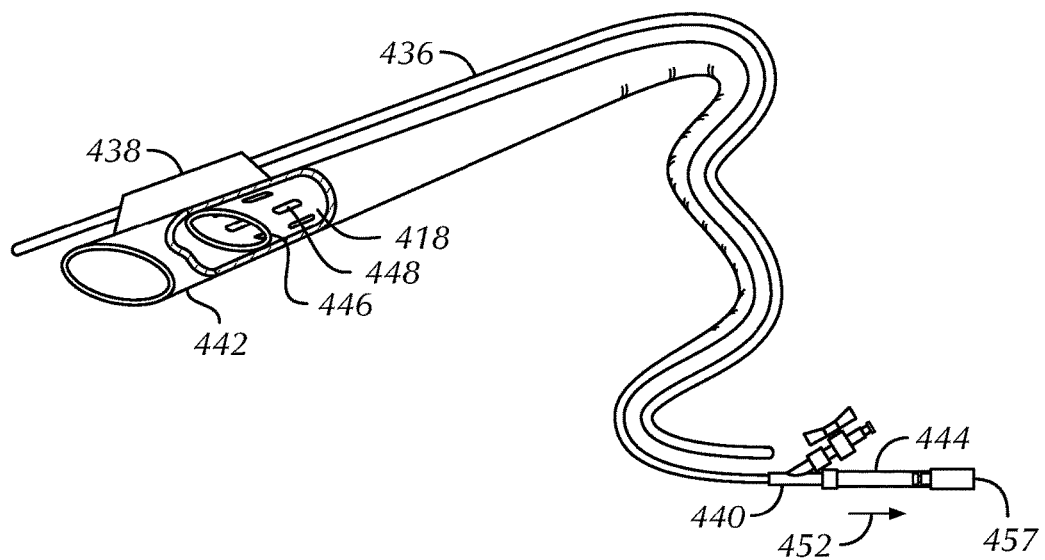
Figure 5:
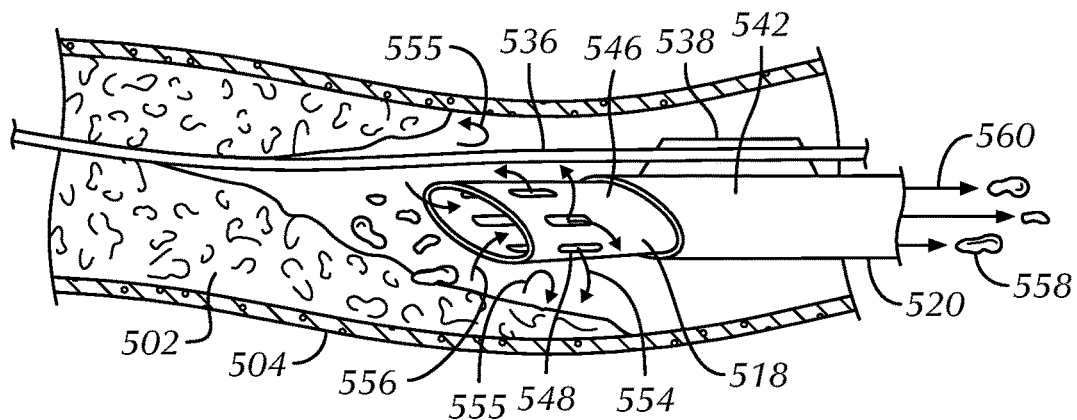
FIG. 5 illustrates a schematic view of obstructive material shearing and bodily fluid turbulence caused by movements of an elongate inner member and one or more orifices in its distal end portion, as constructed in accordance with at least one embodiment.

FIGS. 4A-B illustrate schematic views of an elongate inner member 418 and an elongate outer member 420 advanceable into a vessel or other cavity using a guidewire 436, as constructed in accordance with at least a first embodiment of the present assemblies. As shown in FIG. 5, this first embodiment allows for the shearing of obstructive material that is too large to be removed in whole by the elongate inner member 418. Each of the elongate inner 418 and outer 420 members can extend from a proximal end portion 444, 440 to a distal end portion 446, 442 and can include a lumen therethrough. The distal end portion 446, 442 of one or both of the elongate inner member 418 and the elongate outer member 420 can include a skived opening 451, 453 leading into its respective lumen. A least part of the distal end portion 442 of the elongate outer member 420 can include a sleeve 438 forming a second lumen sized and shaped to receive a portion of the guidewire 436. Alternatively, the second lumen can be integrated within the confines of the outer surface of the elongate outer member 420 (see FIGS. 6A-C). The distal end portion 446 of the elongate inner member 418 can include a wall having a plurality of orifices 448 therethrough. The orifices 448 can produce turbulent flow of bodily fluids during a treatment procedure, which can facilitate removal of obstructive material and can be of various shapes (e.g., round, oval, elliptical, rectangular, triangular or another shape intended to direct bodily fluid flow in a desired direction) and sizes.

The elongate outer member 420 can be disposed concentrically around the elongate inner member 418, which is disposed within the lumen of the elongate outer member 420. The elongate inner 418 and outer 420 members can be arranged such that no appreciable annular gap is provided between the members. Instead, the lumen of the elongate outer member 420 can tightly fit around the outer surface of the elongate inner member 418 without gripping it, thereby allowing proximal 452 and distal 450 movement of the elongate inner member 418 (relative to the elongate outer member 420) while sealing the lumen of the elongate outer member 420. In some examples, the annular gap between the members 418, 420 can be in the range of 0.01 mm to 0.1 mm. A manipulator or handle 457 can be connected to the proximal end portions 444, 440 of one or both of the elongate inner 418 and outer 420 members so that clinicians can easily move the elongate inner member 418 in proximal 452 and distal 450 directions relative to the elongate outer member 420.

A length of the elongate inner member 418 can be greater than a length of the elongate outer member 420, such as from about 2 cm to 10 cm greater in length. The greater length allows the distal end portion 446 of the elongate inner member 418 to extend beyond that of the elongate outer member 420. As illustrated in FIG. 4A, the distal end portion 446 of the elongate inner member 418 can be configured to extend beyond the distal end portion 442 of the elongate outer member 420, while the proximal end portion 444 of the elongate inner member 418 can be configured to concurrently extend proximally of the proximal end portion 440 of the elongate outer member 420. Movement restrictors can be provided at the proximal end portions 444, 440 of the elongate members to restrict excessive movements of the distal end portion 446 of the elongate inner member 418 out of the distal end portion 442 of the elongate outer member 420. As illustrated in FIG. 4B, the distal end portion 446 of the elongate inner member 418 can subsequently be withdrawn into the distal end portion 442 of the elongate outer member 420 when the proximal end portion 444 of the elongate inner member 418 is moved proximally 452.

FIG. 5 illustrates a schematic view of obstructive material 502 shearing and bodily fluid turbulence 555 caused by proximal and distal relative movements between elongate inner 518 and outer 520 members and one or more orifices 548 in a distal end portion 546 of the elongate inner member 518. The distal end portions 546, 542 of the elongate inner 518 and outer 520 members can be guided through a vessel 504 to a site of the obstructive material 502 using a guidewire 536. At this position, relative elongate member 518, 520 movements can provide a mechanical mechanism for shearing and breaking down the obstructive material 502 prior to its aspiration through a lumen of the elongate inner member 518. Blood and other bodily fluid flowing into the distal end portion 546 of the elongate inner member 518 can be discharged 554 through the one or more orifices 548 toward the wall of the vessel 504 to impinge and further break up obstructive material 502 deposits. The bodily fluid turbulence 555 can urge obstructive material particles 558 into 556 and through 560 the lumen of the elongate inner member 518.

A clinician can activate an aspirator in flow communication with a proximal end portion of the elongate inner member 518 to apply a negative pressure to the lumen of the elongate inner member 518. This negative pressure can draw the obstructive material particles 558 proximally toward the aspirator. Through the combined action of the obstructive material 502 shearing, bodily fluid turbulence 555, and proximal drawing of obstructive material particles 558, the vessel 504 can be adequately treated without having to remove the elongate members 518, 520 from the patient's body mid-procedure to be unplugged or otherwise cleaned before continued use. Once the obstructive material 502 is adequately captured and removed, the distal end portions 546, 542 of the elongate inner 518 and outer 520 members can be advanced to a new treatment site and used to break down, capture, and remove other obstructive material.

Figure 6A:
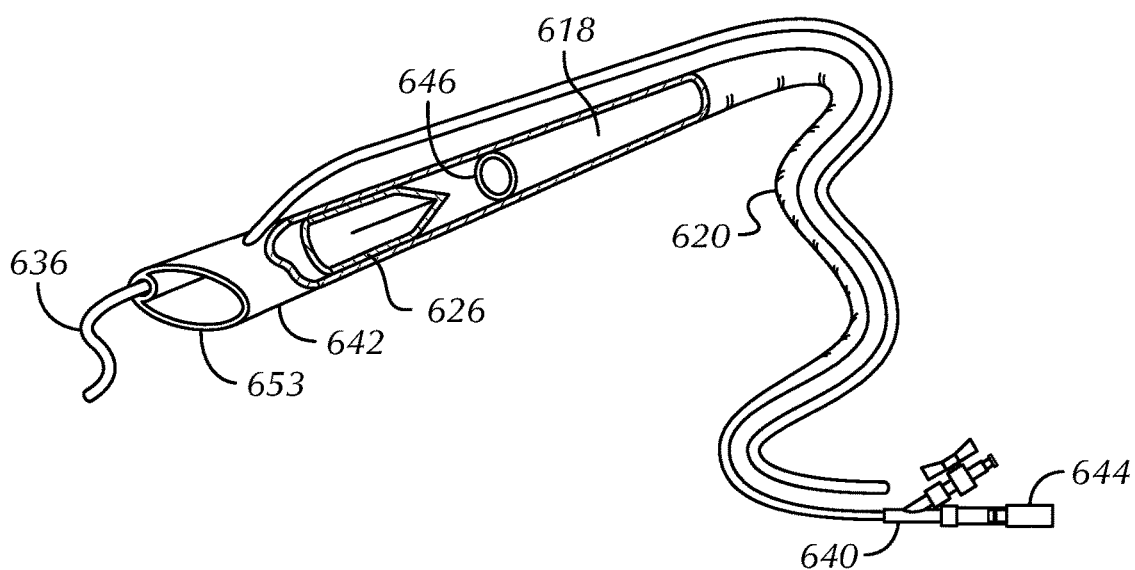
FIGS. 6A-C illustrate schematic views of relative movements between an elongate inner member and an elongate outer member, as constructed in accordance with at least one embodiment.
Figure 6B:
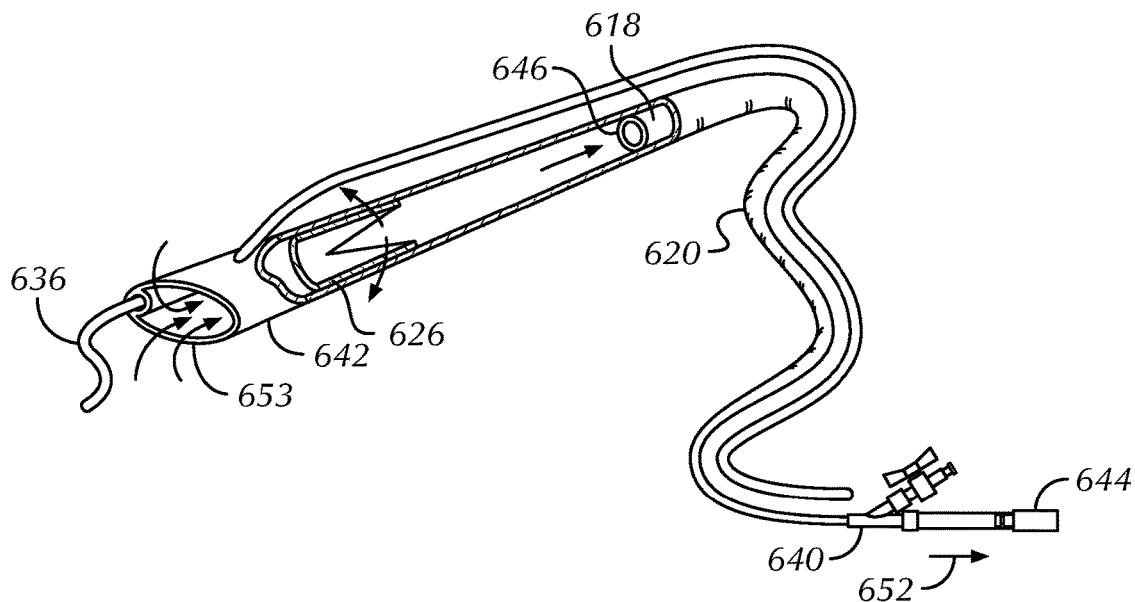
Figure 6C:
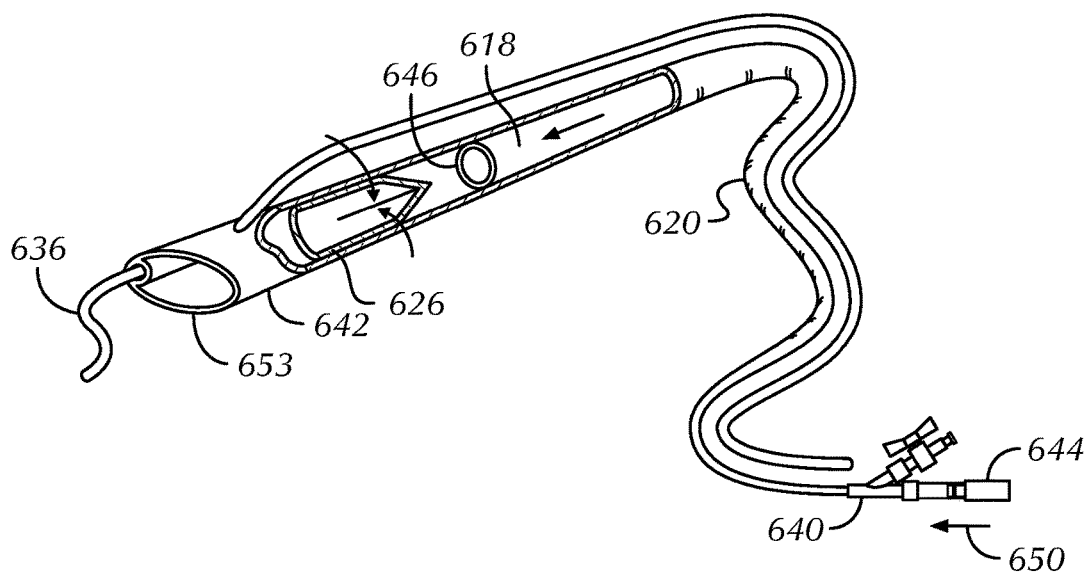

FIGS. 6A-C illustrate schematic views of an elongate inner member 618 and an elongate outer member 620 advanceable into a vessel or other cavity over a guidewire 636, as constructed in accordance with at least a second embodiment of the present assemblies. This second embodiment allows for the creation of suction at a distal end portion 646 of the elongate inner member 618 to help pull the obstructive material into and through the member. Similar to the first embodiment illustrated in FIGS. 4A-B and 5, each of the elongate inner 618 and outer 620 members can extend from a proximal end portion 644, 640 to a distal end portion 646, 642 and can include a lumen therethrough. The distal end portion 642 of at least the elongate outer member 620 can include a skived opening 653 leading into its lumen. The distal end portions 646, 642 of the elongate inner 618 and outer 620 members can be guided through the vessel or cavity to a site of the obstructive material.

The elongate outer member 620 can be disposed concentrically around the elongate inner member 618, which can be disposed within the lumen of the elongate outer member 620. The elongate inner 618 and outer 620 members can be arranged such that the lumen of the elongate outer member 620 tightly fits around the outer surface of the elongate inner member 618 without gripping it, thereby allowing proximal 652 and distal 650 movements of the elongate inner member 618 (relative to the elongate outer member 620) while sealing the lumen of the elongate outer member 620.

A length of the elongate inner member 618 can be configured such that the distal end portion 646 of the elongate inner member 618 extends within the distal end portion 642 of the elongate outer member 620, while the proximal end portion 644 of the elongate inner member 618 extends proximally of the proximal end portion 640 of the elongate outer member 620. A one-way valve 626 can be positioned within the distal end portion 642 of the elongate outer member 620, adjacent and distal to the distal end portion 646 of the elongate inner member 618.

Relative elongate member 618, 620 movements can provide a mechanical mechanism for urging obstructive material into and through the lumen of the elongate inner member 618. The one-way valve 626 can be configured to move from a closed position (see FIG. 6A) to an open position (see FIG. 6B) in response to a predetermined negative pressure level created by the relative movements of the elongate members 618, 620 and/or activation of an aspirator 614 in flow communication with a proximal end portion 644 of the elongate inner member 618. The negative pressure can draw the obstructive material proximally. For example, the one-way valve 626 can be caused to move from the closed position to the open position through retraction (or proximal movement 652) of the elongate inner member 618 relative to the elongate outer member 620. This retraction of the elongate inner member 618 creates a cavity to receive obstructive material, flowing from a location distal of the one-way valve 626 to a location proximal of the valve, between the distal end portion 646 of the elongate inner member 618 and the one-way valve 626. Subsequent advancement (or distal movement 650) of the elongate inner member 618 relative to the elongate outer member 620 can cause the one-way valve 626 to move from the open position (see FIG. 6B) to the closed position (see FIG. 6C) and can further cause the obstructive material proximal of the valve 626 to be urged through the lumen of the elongate inner member 618 toward its proximal end portion 644. Once the obstructive material is captured and removed (e.g., by being directed to a waste collection reservoir), the distal end portions 646, 642 of the elongate inner 618 and outer 620 members can be advanced to a new treatment site and used to capture and remove other obstructive material.

The ability to distally create negative pressure through relative elongate member 618, 620 movements can provide an assembly with a number of advantages. First, a clinician using the assembly does not need to rely on activation of a proximally-positioned aspirator for the negative pressure used to capture and remove obstructive material. Second, transmission losses associated with negative pressure created at a proximal end portion of the assembly can be avoided. Third, the strength and profile of the negative pressure felt by obstructive material at a treatment site and urged into the assembly can be enhanced through the combined efforts of relative elongate member movements and aspirator activation.

Figure 7:
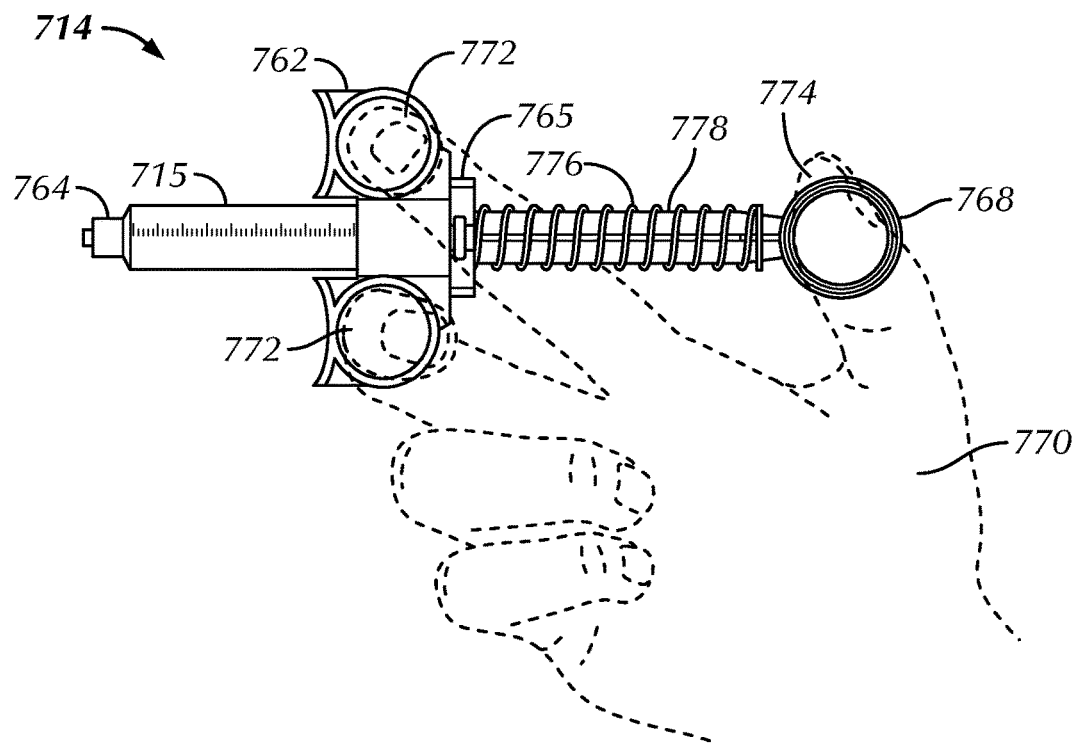
FIGS. 7-8 illustrate aspirators for creating negative and positive pressures at a proximal end portion of an elongate inner member, as constructed in accordance with at least two embodiments.
Figure 8:
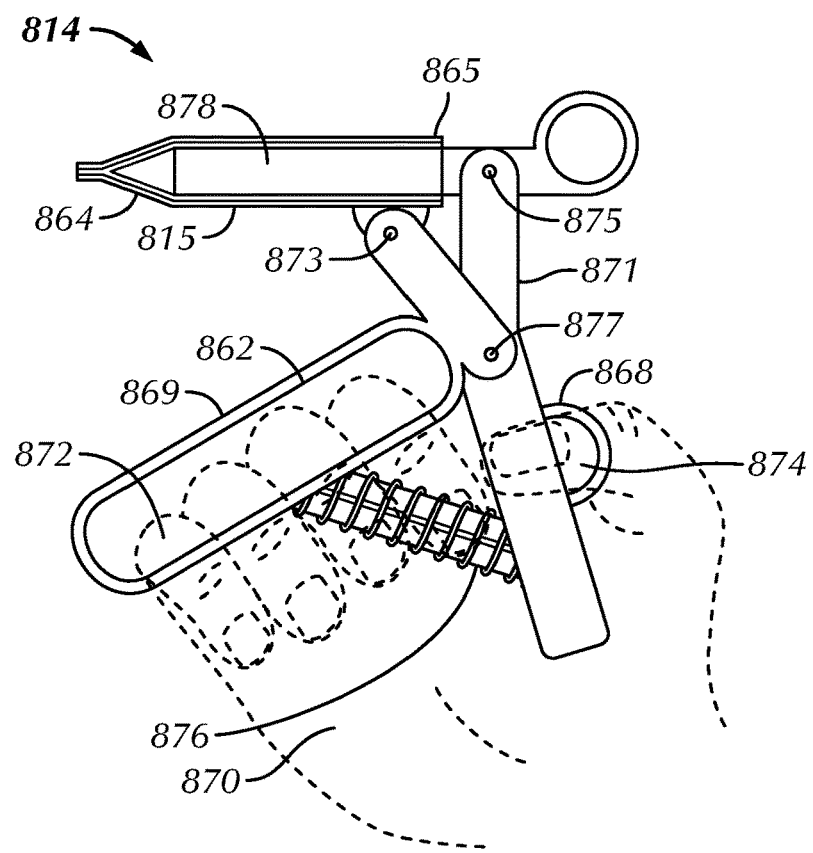

FIGS. 7 and 8 illustrate aspirators 714, 814 for coupling to a proximal end portion of an elongate inner member. The aspirators 714, 814 can be used to create proximally-directed negative pressure and distally-directed positive pressure. Each aspirator 714, 814 can include a syringe barrel 715, 815, a plunger 778, 878 slidable in the syringe barrel, and a resilient means 776, 876 configured to urge the plunger toward a resting position. The syringe barrel 715, 815 can extend from a proximal end 765, 865 to a distal end 764, 864. Along the majority of its length, the syringe barrel 715, 815 can be substantially uniform in both cross-sectional shape and cross-sectional dimension. The distal end 764, 864 of the syringe barrel 715, 815 can be tapered. The distal end 764, 864 of the syringe barrel 715, 815 can be coupled to the proximal end portion of the elongate inner member directly or indirectly via a valve manifold (FIG. 3). The plunger 778, 878 can be an elongate member with a tip at its distal end. The resilient means 776, 876 can include a spring member. In the example of FIG. 7, the spring member is configured to urge the plunger 778 to a resting position in which the plunger's tip is at a retracted position in the syringe barrel 715. In the example of FIG. 8, the spring member is configured to urge the plunger 878 to a resting position in which the plunger's tip is at a depressed position in the syringe barrel 815.

The aspirators 714, 814 can be controlled by a single hand 770, 870 of the clinician, such as through converging movements of fingers 772, 872 and a thumb 774, 874. Finger and thumb rings can be configured to facilitate the converging movements. In the example of FIG. 7, when the tip of the plunger 778 is fully or almost fully retracted out of the syringe barrel 715, finger 762 and thumb 768 rings are spaced apart from one another on telescopically slidable members, with the finger rings 762 positioned on the proximal end 765 of the syringe barrel 715 and the thumb ring 768 positioned on the proximal end of the plunger 778. In the example of FIG. 8, when the tip of the plunger 878 is fully or almost fully depressed within the syringe barrel 815, finger 862 and thumb 868 rings are spaced apart from one another on a scissor-grip handle that includes two members 869, 871 and three pivot connection points 873, 875, 877. The first pivot connection point 873 can be between the first handle member 869 and the syringe barrel 815. The second pivot connection point 875 can be between the second handle member 871 and the plunger 815. And the third pivot connection point 877 can be between the first 869 and second 871 handle members. Optionally, one or both of the handle members 869, 871 can be bent to facilitate being gripped by the clinician. The shapes of the handle members 869, 871 and placement of the pivot connection points 873, 875, 877 can provide leverage to decrease the amount of force that must be exerted by the clinician's hand to move the plunger 878 relative to the syringe barrel 815.

Converging movements of the clinician's fingers 772, 872 and thumb 774, 874 can cause the plunger 778, 878 to be advanced into the syringe barrel 715 (see FIG. 7) or retracted out of the syringe barrel 815 (see FIG. 8). In each case, the resilient means 776, 876 urges the tip of the plunger 778, 878 back to its predetermined resting position. When the plunger 778, 878 is retracted out of the syringe barrel 715, 815, negative pressure is created at the distal end 764, 864 of the syringe barrel 715, 815 that draws obstructive material and bodily fluid through a lumen of the elongate inner member and into the syringe barrel 715, 815. When the plunger 778, 878 is advanced (or depressed) into the syringe barrel 715, 815, positive pressure is created at the distal end 764, 864 of the syringe barrel 715, 815 that urges the obstructive material and bodily fluid within the syringe barrel 715, 815 toward a waste collection reservoir. The amount of negative or positive pressure created by the aspirator 714, 814 can be controlled by controlling the distance that the fingers 772, 872 and thumb 774, 874 are forced together.

Figure 9:
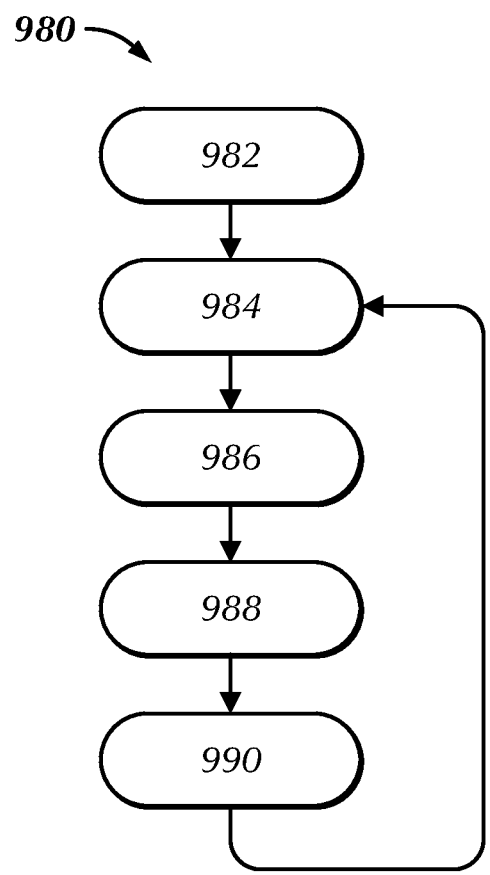
FIG. 9 illustrates a method of breaking down, capturing, and removing obstructive materials from a body vessel or other cavity, as constructed in accordance with at least one embodiment.

FIG. 9 illustrates a method 980 of breaking down, capturing, and removing obstructive materials from a body vessel or other cavity. At 982, a distal end of an assembly, including (among other things) an elongate inner member and a surrounding elongate outer member, can be advanced to a first location within the vessel or cavity proximate to obstructive material to be removed. The distal end of the assembly can be guided to the first location along a pre-advanced guidewire. In an example, the first location is within a peripheral vessel. In another example, the first location is within a pulmonary artery.

Obstructive material at different locations within the body can be very different from one another. For example, some obstructive material can remain cohesive on removal, while other materials easily break up into smaller portions when any removal force (negative pressure) is applied to them. With existing catheter-based capture devices, a clinician may have to carry out a number of removal operations in order to remove a single site of obstructive material, each operation involving the introduction of the capture device, capture of part of the obstructive material, and removal of the device from the patient. Repetition of these introduction and removal steps can be time consuming and can cause discomfort for the patient.

The present methods allow obstructive material at a site within the body to be adequately removed during a single introduction procedure by leveraging relative movements between the elongate inner and outer members, at 984. In an example, moving the elongate inner member relative to the elongate outer member can include cutting, fragmenting, or otherwise breaking down the obstructive material before aspirating it. The elongate inner member can include a length greater than a length of the elongate outer member, thereby allowing the distal end of the elongate inner member to be moved distally and extend beyond that of the elongate outer member to shear the obstructive material. In another example, moving the elongate inner member relative to the elongate outer member can include creating negative pressure near the distal end of the assembly to draw the obstructive material into and through a lumen of the elongate inner member. When the elongate inner member is retracted (or moved proximally), negative pressure at the distal end of the assembly can result.

At 986, an aspirator in flow communication with a proximal end of the elongate inner member can be activated to create negative pressure and draw obstructive material through the lumen of the elongate inner member. The aspirator can be activated to create negative pressure prior to, concurrently with, or after movements of the elongate inner member relative to the elongate outer member. After the obstructive material is moved through the elongate inner member to a syringe barrel of the aspirator, the aspirator, at 988, can be activated to create positive pressure and urge the obstructive material into a waste collection reservoir.

At 990, the assembly can be moved from the first location to a different second location proximate to other obstructive material to be removed without having to withdraw and reintroduce the assembly. At the second location, method steps 984, 986 and 988 can be repeated.

Closing Notes:

The present assemblies and methods can be used to break down, capture, and remove obstructive material without requiring expensive capital equipment and maintenance and without the need for surgical intervention. A number of obstructive materials can be removed from a number of different sites within a patient's body before the assembly is removed. Relative movements between elongate inner and outer members can break down and/or capture obstructive material within a lumen of the elongate inner member via a prolonged or distally-created suction profile. An aspiration source in flow communication with the lumen of the elongate inner member can move the obstructive material through such lumen and toward a waste collection reservoir.

The above Detailed Description includes references to the accompanying drawings, which form a part of the Detailed Description. The Detailed Description should be read with reference to the drawings. The drawings show, by way of illustration, specific embodiments in which the present assemblies and methods can be practiced. These embodiments are also referred to herein as "examples."

The Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Also, various features or components have been or can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, an assembly for removing obstructive material from a body vessel or other cavity can include an elongate inner member, an elongate outer member, and an aspirator. Each of the elongate members can extend from a proximal end portion to a distal end portion and can include a lumen therethrough. The elongate inner member can have a wall including a plurality of orifices at its distal end portion and can be partially disposed in the lumen of the elongate outer member. The elongate inner member can be moveable along its longitudinal axis relative to the elongate outer member such that the plurality of orifices is extendable beyond, and retractable within, the distal end portion of the elongate outer member. The aspirator can be in flow communication with the elongate inner member for drawing the obstructive material into and through the lumen of the elongate inner member.

In Example 2, the assembly of Example 1 can optionally further comprise a first one-way valve and a second one-way valve. The first one-way valve can be in communication with the lumen of the elongate inner member to allow flow in a distal-to-proximal direction toward the aspirator. The second one-way valve can allow flow in a direction away from the aspirator and toward a waste collection reservoir.

In Example 3, the assembly of any one of Examples 1 or 2 can optionally further comprise a manipulator handle coupled to the proximal end portion of one or both of the elongate inner member and the elongate outer member to allow advancement and retraction of the elongate inner member relative to the elongate outer member.

In Example 4, the assembly of any one or any combination of Examples 1-3 can optionally further comprise a radiopaque marker positioned on the distal end portion of one or both of the elongate inner member and the elongate outer member.

In Example 5, the assembly of any one or any combination of Examples 1-4 can optionally be configured such that the lumen of the elongate outer member tightly fits around the outer surface of the elongate inner member without gripping it, thereby allowing the elongate inner member to move relative to the elongate outer member while sealing the lumen of the elongate outer member.

In Example 6, the assembly of any one or any combination of Examples 1-5 can optionally be configured such that a wall of the elongate outer member includes a reinforcing layer composed of braided or wound fibers.

In Example 7, the assembly of any one or any combination of Examples 1-6 can optionally be configured such that the distal end portion of the elongate outer member includes a second lumen, which is non-coaxial with its other lumen and is sized and shaped to receive a portion of a guidewire.

In Example 8, the assembly of any one or any combination of Examples 1-7 can optionally be configured such that the distal end portion of one or both of the elongate inner member and the elongate outer member includes a skived distal tip opening into its lumen.

In Example 9, the assembly of any one or any combination of Examples 1-8 can optionally be configured such that the plurality of orifices includes at least three radially-spaced orifices, each orifice having an oval or elliptical shape.

In Example 10, the assembly of any one or any combination of Examples 1-9 can optionally be configured such that the aspirator includes a syringe barrel, a plunger slidable in the syringe barrel, and a resilient means, the resilient means configured to urge the plunger toward a resting position.

In Example 11, an assembly for removing obstructive material from a body vessel or other cavity can include an elongate inner member and an elongate outer member. Each of the elongate members can extend from a proximal end portion to a distal end portion and can include a lumen therethrough. The elongate inner member can be partially disposed in the lumen of the elongate outer member and can be moveable along its longitudinal axis relative to the elongate outer member such that its distal end portion is extendable beyond, and retractable within, the distal end portion of the elongate outer member. The elongate outer member can include a second lumen at its distal end portion. The second lumen can be non-coaxial with the lumen in which the elongate inner member is disposed and sized and shaped to receive a portion of a guidewire.

In Example 12, the assembly of Example 11 can optionally further comprise an aspirator in flow communication with the elongate inner member for drawing the obstructive material through the lumen of the elongate inner member.

In Example 13, the assembly of Example 12 can optionally be configured such that the aspirator includes a syringe barrel, a plunger slidable in the syringe barrel, and a resilient means. The resilient means can be configured to urge the plunger toward a resting position.

In Example 14, the assembly of any one of Examples 11 or 12 can optionally further comprise a first one-way valve and a second one-way valve. The first one-way valve can be in communication with the lumen of the elongate inner member to allow flow in a distal-to-proximal direction toward the aspirator. The second one-way valve can allow flow in a direction away from the aspirator and toward a waste collection reservoir.

In Example 15, the assembly of any one or any combination of Examples 11-14 can optionally further comprise a manipulator handle coupled to the proximal end portion of one or both of the elongate inner member and the elongate outer member to allow advancement and retraction of the elongate inner member relative to the elongate outer member.

In Example 16, the assembly of any one or any combination of Examples 11-15 can optionally be configured such that the elongate inner member has a wall including an orifice at its distal end portion. The orifice can have an axis extending at an angle to an extension axis of the elongate inner member.

In Example 17, a method for removing obstructive material from a first location with a body vessel or cavity can include percutaneously advancing a distal end of an assembly, which includes an elongate inner member and a surrounding elongate outer member, to the first location. The elongate inner member can be moved relative to the elongate outer member along its longitudinal axis. This movement can include axially reciprocating a distal end of the elongate inner member between positions beyond and within a distal end of the elongate outer member. An aspirator in flow communication with a lumen of the elongate inner member can be activated by sliding a plunger relative to a syringe barrel and allowing a resilient member to urge the plunger toward a resting position.

In Example 18, the method of Example 17 can optionally be configured such that percutaneously advancing the distal end of the assembly to the first location includes advancing a guidewire lumen of the elongate outer member along a pre-advanced guidewire.

In Example 19, the method of any one of Examples 17 or 18 can optionally be configured such that axially reciprocating the distal end of the elongate inner member between positions beyond and within the distal end of the elongate outer member includes cutting or fragmenting the obstructive material prior to aspirating it.

In Example 20, the method of any one or any combination of Examples 17-19 can optionally be configured such that axially reciprocating the distal end of the elongate inner member between positions beyond and within the distal end of the elongate outer member includes producing a turbulent flow of bodily fluid through movement of a plurality of orifices in a wall of the distal end portion of the elongate inner member.

In Example 21, the method of any one or any combination of Examples 17-20 can optionally be configured such that removing the obstructive material includes depositing the obstructive material into a waste collection reservoir in flow communication with the aspirator.

In Example 22, the method of any one or any combination of Examples 17-21 can optionally further comprise moving the assembly from the first location to a different second location proximate to other obstructive material to be removed without having to withdraw and reintroduce the assembly from the body vessel or cavity. When at the second location, the elongate inner member can be moved relative to the elongate outer member along its longitudinal axis and the aspirator can be activated, thereby removing the obstructive material.

In Example 23, the assembly or method of any one or any combination of Examples 1-22 can optionally be configured such that all components or options recited are available to use or select from.

Certain terms are used throughout this patent document to refer to particular features or components. As one skilled in the art will appreciate, different persons may refer to the same feature or component by different names. This patent document does not intend to distinguish between components or features that differ in name but not in function.

For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." The terms "distal" and "proximal" are used to refer to a position or direction relative to a treating clinician. "Distal" or "distally" refer to a position that is further from the treating clinician. Similarly, "advance," "advancing," or "depressed" refer to a direction away from the treating clinician. "Proximal" and "proximally" refer to a position that is closer to the treating clinician. Similarly, "retract" or "retracting" refer to a direction toward the treating clinician. The term "patient" refers to a human patient or an animal patient. The term "clinician" refers to a doctor, nurse or other care provider and can include support personnel.

The scope of the invention should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, an assembly, kit or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects. It is to be understood that although dependent claims may be set out in single dependent form, the features of these claims can be combined as if the claims were in multiple dependent form.

The Abstract is provided to allow the reader to quickly ascertain the nature of the technical disclosure. It is submitted with the understanding that it will not be used to interpret or limit the scope or meaning of the claims.

What is claimed is:

1. An assembly for removing obstructive material from a body vessel or cavity, comprising:
   an elongate outer member and an elongate inner member, each extending from a proximal end to a distal end and including a first lumen therethrough, wherein a maximum annular gap between an inner surface of the elongate outer member and an outer surface of the elongate inner member is 0.1 mm,
   the first lumen of the elongate inner member having an aspiration entrance at the distal end of the elongate inner member and defined by a wall, the wall including a plurality of orifices adjacent and proximal to the entrance,
   the elongate inner member movable along a common longitudinal axis relative to the elongate outer member such that the plurality of orifices is extendable beyond, and retractable within, the distal end of the elongate outer member to break down the obstructive material, wherein the elongate outer member does not include a wall orifice;
   the elongate outer member including a second lumen positioned about its outer surface, the second lumen providing a longitudinal slot or channel adapted for a guidewire;
   an aspirator in flow communication with the elongate inner member for drawing the obstructive material through the aspiration entrance of the first lumen of the elongate inner member; and
   a valve manifold comprising a first port, the first port including a one-way valve in communication with the first lumen of the elongate inner member and allowing flow in a distal-to-proximal direction toward the aspirator.

2. The assembly of claim 1, further comprising a second port within the valve manifold, the second port including a second one-way valve allowing flow in a direction away from the aspirator and toward a waste collection reservoir.

3. The assembly of claim 2, wherein the one-way valve and second one-way valve are positioned proximal of the proximal end of the elongate inner member.

4. The assembly of claim 1, further comprising a manipulator handle coupled to the proximal end of one or both of the elongate inner member and the elongate outer member to allow advancement and retraction of the elongate inner member relative to the elongate outer member.

5. The assembly of claim 4, wherein the manipulator handle is configured to advance and retract the elongate inner member relative to the elongate outer member while the aspirator draws the obstructive material through the aspiration entrance of the first lumen of the elongate inner member.

6. The assembly of claim 1, further comprising a radiopaque marker positioned adjacent to the distal end of one or both of the elongate inner member and the elongate outer member.

7. The assembly of claim 1, wherein the first lumen of the elongate outer member tightly fits around the outer surface of the elongate inner member without gripping it and allows the elongate inner member to move relative to the elongate outer member while sealing the first lumen of the elongate outer member.

8. The assembly of claim 1, wherein a wall of the elongate outer member includes a reinforcing layer composed of braided or wound fibers.

9. The assembly of claim 1, wherein a longitudinal axis of the second lumen is spaced from the common longitudinal axis of the elongate inner and outer members.

10. The assembly of claim 1, wherein the distal end of one or both of the elongate inner member and the elongate outer member includes a skived distal tip opening into its first lumen.

11. The assembly of claim 1, wherein the plurality of orifices is radially-spaced around the wall of the elongate inner member and each orifice has an oval or elliptical shape.

12. The assembly of claim 1, wherein the aspirator includes a syringe barrel, a plunger slidable in the syringe barrel, and a resilient means, the resilient means configured to urge the plunger toward a resting position.

13. The assembly of claim 1, wherein the distal end of the elongate inner member is configured to extend beyond the distal end of the elongate outer member, and wherein the proximal end of the elongate inner member is configured to concurrently extend proximally of the proximal end of the elongate outer member.

14. The assembly of claim 1, wherein the distal end of the elongate inner member is configured to be retracted into the distal end of the elongate outer member.

15. The assembly of claim 1, wherein the elongate outer member includes a pre-curved configuration in its unbiased state.

16. The assembly of claim 1, wherein a distal end portion of the elongate outer member includes a sleeve attached to the outer surface of the elongate outer member and forming the second lumen.

17. The assembly of claim 1, wherein a length of the second lumen of the elongate outer member is less than a length of the first lumen of each of the elongate inner and outer members.

* * * * *